United States Patent [19]

November

[11] 4,041,769
[45] Aug. 16, 1977

[54] DENSITOMETER

[75] Inventor: Milton H. November, Hacienda Heights, Calif.

[73] Assignee: International Telephone and Telegraph Corporation, New York, N.Y.

[21] Appl. No.: 729,779

[22] Filed: Oct. 5, 1976

[51] Int. Cl.² .............................................. G01N 9/00
[52] U.S. Cl. .................................................. 73/32 A
[58] Field of Search ......................... 73/32 A; 310/26

[56] References Cited

U.S. PATENT DOCUMENTS

| 2,826,706 | 3/1958 | Sackett | 310/26 |
| 2,978,670 | 4/1961 | Peek | 310/26 X |
| 3,808,875 | 5/1974 | Miller | 73/32 A |

Primary Examiner—James J. Gill
Attorney, Agent, or Firm—A. Donald Stolzy

[57] ABSTRACT

A vibration densitometer having a permanent magnet biased magnetostrictive drive unit.

3 Claims, 3 Drawing Figures

DENSITOMETER

BACKGROUND OF THE INVENTION

This invention relates to densitometers, and more particularly to permanent magnet biased vibration densitometers. Such is known in other arts, but not in the vibration densitometer art.

SUMMARY OF THE INVENTION

In accordance with the present invention a permanent magnet bias (old by itself in the art) is employed to provide input-output synchronism to effect oscillation.

The above-described and other advantages of the present invention will be better understood from the following detailed description when considered in connection with the accompanying drawings.

BRIEF DESCRIPTION OF THE DRAWINGS

In the drawings, which are to be regarded as merely illustrative.

DESCRIPTION OF THE PREFERRED EMBODIMENTS

Figure 1:
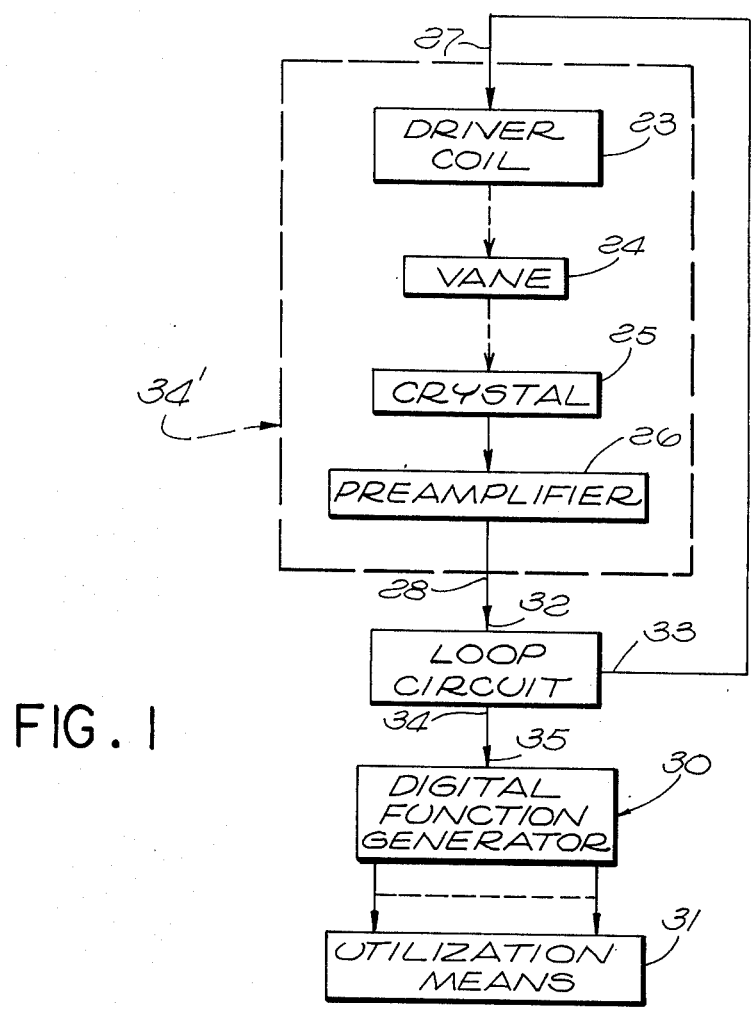
FIG. 1 is a block diagram of a densitometer constructed in accordance with the present invention.
Figure 3:
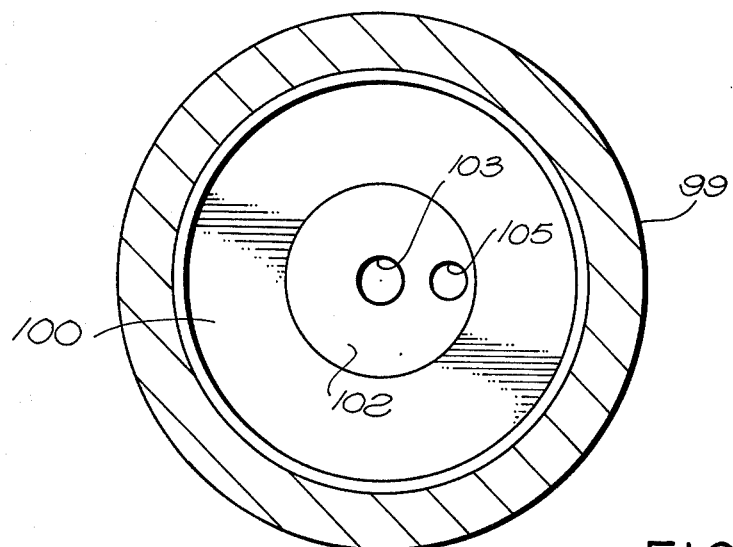
FIG. 3 is a view taken on the line 3—3 shown in FIG. 2.

In the drawings, in FIG. 1, a vibration densitometer probe is indicated at 34' having a driver coil 23, a vane 24, a piezoelectric crystal 25 and a preamplifier 26.

34' has an input lead 27 and an output lead 28.

Other blocks shown in FIG. 1 are a loop circuit 29, a digital function generator 30 and utilization means 31. Loop circuit 29 has an input lead 32 and output leads 33 and 34. Digital function generator 30 has an input lead 35 connected from loop circuit output lead 34. The output of digital function generator 30 is connected to utilization means 31.

The output lead 28 of probe 34' is connected to the input lead 32 of loop circuit 29. The input lead 27 of probe 34' is connected from the output lead 33 of loop circuit 29. Probe 34' and loop circuit 29 form a closed loop electromechanical oscillator. Vane 24 is submerged in a fluid. The density of the fluid is a function of frequency at which vane 24 vibrates. For the theory of operation, see U.S. Pat. Nos. 3,878,374 and 3,958,446 issued Apr. 15, 1975, and May 25, 1976, respectively.

Digital function generator 30 may have its input lead 35 connected from lead 33 or at other points in loop circuit 29. Loop circuit 29 impresses a square wave voltage on input lead 35 of digital function generator 30 having a mark-to-space ratio of 1:1.

Utilization means 31 shown in FIG. 1 may be a density indicator, a specific gravity indicator, a process controller or otherwise. Digital function generator 30 thus produces an output directly proportional to density or specific gravity in the manner described in the said U.S. Pat. No. 3,878,374.

Throughout this description, reference will be made to the text of certain U.S. patents. These patents are listed for convenience below.
1. U.S. Pat. No. 3,677,067.
2. U.S. Pat. No. 3,706,220.
3. U.S. Pat. No. 3,738,155.
4. U.S. Pat. No. 3,741,000.
5. U.S. Pat. No. 3,878,374.
6. U.S. Pat. No. 3,958,446.

The foregoing patents of paragraphs (1), (2), (3), (4), (5) and (6) are hereinafter referred to as patents P1, P2, P3, P4, P5 and P6, respectively.

Probe 34' shown in FIG. 1 may be conventional except as noted hereinafter. Alternatively, probe 34' may be similar to a probe shown in any of the patents P1-P6 except as noted hereinafter.

Preamplifier 26 shown in FIG. 1 may be conventional.

OPERATION

In the embodiment of the invention shown in FIG. 1, probe 34' and loop circuit 29 provide an electromechanical oscillator which oscillates at a frequency dependent upon the density of the fluid in which vane 24 is immersed. The same is true of the pulse repetition frequency of the square wave voltage applied to the input lead 35 of digital function generator 30.

Figure 2:
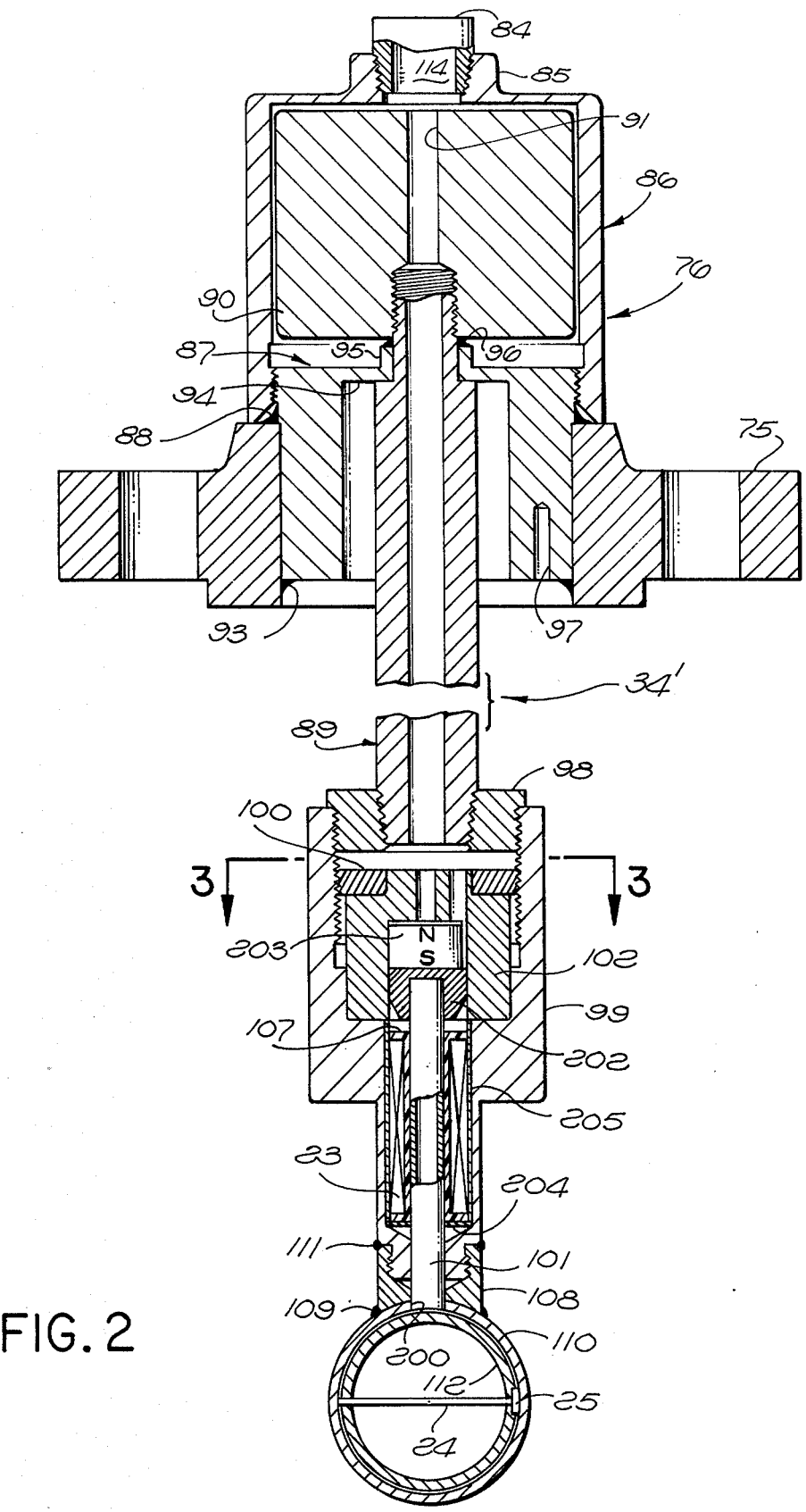
FIG. 2 is a vertical sectional view through the densitometer probe.

The manner in which probe 34' of FIG. 2 fits into a pipeline is explained in U.S. Pat. No. 3,958,446. See flange 75.

A vertical sectional view of probe 34' is shown in FIG. 2 where assembly 76 includes a nipple 84 threaded into a hollow cylindrical projection 85 of an end cap 86. End cap 86 is threaded to a body 87. Flange 75, end cap 86 and body 87 are welded or soldered together at 88. A hollow shaft 89 is externally threaded into a cylinder 90 that is solid except for a hole 91 which extends completely therethrough and is in communication with the hollow interior 92 of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pin hole 97, if desired, so that it may be held while end cap 86 is turned or threaded thereto.

Shaft 89 is, in turn, fixed to a ferrule 98 by being threaded thereinto. Ferrule 98, in turn, is fixed to a body 99 by being threaded thereinto.

A ring 100 is threaded into body 99. A magnetostrictive tube 101 which is hollow and open at both ends is slidable in a hole 200 through a cylinder 110 and press fit into a soft iron plug 202 that is, in turn, press fit into a body 102. A permanent magnet 203 is fixed in body 102. Body 102 may have holes 103 and 105 to below plug 202. See U.S. Pat. No. 3,958,446. Driver coil 23 is shown again in FIG. 2 on a dielectric spool 107 press fit onto tube 101. A ferrule 108 is welded at 109 to cylinder 110. Body 99 is threaded into ferrule 108 and welded thereto at 111. Tube 101 bears against the external cylindrical surface of a cylinder 112. Vane 24 is fixed inside cylinder 110 in a manner identical to that illustrated in several patents including but not limited to U.S. Pat. No. 3,677,067. The same is true of crystal 25.

Cylinders 110 and 112, vane 24, and crystal 25 may be identical to those disclosed in the last mentioned patent, if desired. Tube 101 is slidable through the lower end of body 99 and is slidable through the circular holes in ferrule 108 and cylinder 110.

A ferromagnetic washer is provided at 204. A ferromagnetic cylinder is provided at 205.

A more detailed explanation of the operation of a vibration densitometer employing the structure disclosed herein is set forth in all the patents cited herein.

It is common to use a preamplifier in the probe. Such a preamplifier may be employed at 114 in FIG. 2, or at any other convenient location, as desired.

Magnet 203 is constructed so as to cause vane 24 to be vibrated at the output frequency of crystal 25. In FIG. 1, lead 33 may or may not carry a signal having a component of D.C. voltage or current, or only A.C.

Magnet 203 may be poled as shown or poled in the opposite direction.

What is claimed is:

1. A vibration densitometer comprising: a probe having input and output leads; and a loop circuit having output and input leads connected respectively from and to said probe input and output leads, said probe having a magnetostrictive driver including a magnetostrictive tube, a coil mounted around said tube, said coil being connected from said probe input lead, and a permanent magnet fixed relative to one end of said tube to oppose the magnetic flux created by said coil by the flow of current therein in one direction, a vane to be vibrated by said tube, and means connected to said probe output lead responsive to vane vibrations to produce an electrical A.C. signal synchronously therewith and to impress the same on said coil, said probe and said loop circuit forming an electromechanical oscillator whose resonant frequency is a function of the density of the fluid in which said vane is immersed, said opposition to said magnetic flux allowing said flux to vary, but biasing the same in a manner such that it does not substantially reverse directions during the positive and negative swings of said A.C. signal so that the probe output lead has a signal with a frequency the same as that on the probe input lead.

2. The invention as defined in claim 1, wherein a digital function generator and utilization means are connected in succession in that order from said loop circuit, said digital function generator producing an output to said utilization means directly proportional to density, said loop circuit impressing a signal on said digital function generator, the frequency of which is a function of the density in which said vane is immersed.

3. The invention as defined in claim 2, wherein said utilization means includes a density indicator.

* * * * *